(12) United States Patent
Giles et al.

(10) Patent No.: US 6,914,241 B2
(45) Date of Patent: *Jul. 5, 2005

(54) MASS SPECTROMETER

(75) Inventors: Kevin Giles, Altrincham (GB); John Brian Hoyes, Stockport (GB); Steve Pringle, Darwen (GB); Jason Lee Wildgoose, Stockport (GB)

(73) Assignee: Micromass UK Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/868,934

(22) Filed: Jun. 17, 2004

(65) Prior Publication Data

US 2004/0227071 A1 Nov. 18, 2004

Related U.S. Application Data

(63) Continuation of application No. 10/603,824, filed on Jun. 26, 2003, now Pat. No. 6,791,078.
(60) Provisional application No. 60/422,134, filed on Oct. 30, 2002.

(30) Foreign Application Priority Data

| Jun. 27, 2002 | (GB) | ............................................. | 0214898 |
| Feb. 11, 2003 | (GB) | ............................................. | 0303055 |
| Apr. 11, 2003 | (GB) | ............................................. | 0308419 |

(51) Int. Cl.$^7$ ............................................. H01J 49/40

(52) U.S. Cl. ....................... 250/286; 250/281; 250/282; 250/287

(58) Field of Search ................................ 250/286, 281, 250/282, 287

(56) References Cited

U.S. PATENT DOCUMENTS

| 3,778,678 A | 12/1973 | Masuda |
| 3,806,763 A | 4/1974 | Masuda |
| 3,872,361 A | 3/1975 | Masuda |

(Continued)

FOREIGN PATENT DOCUMENTS

| CA | 2281405 | 3/2000 |
| GB | 2375653 | 11/2002 |
| GB | 2 381 948 A | 5/2003 |

(Continued)

OTHER PUBLICATIONS

Schwager et al., "The Solitron—A New Spectrometer That Uses the Mass Selectivity of a Solitary, Traveling Electric Potential Hill", $42^{nd}$ ASMS Conference on Mass Spectrometry, pp. 512, 1994.

Hu et al., "Design of a Traveling–Wave Field Panel for Pharmaceutical Powders Based on Computer Simulation of Particle Trajectories", IEEE Transactions on Industry Applications, vol. 33, No. 3, pp. 641–650, 1997.

Masuda et al., "Approximate Methods For Calculating a Non–Uniform Travelling Field", Journal of Electrostatics, vol. 1, pp. 351–370, 1975.

(Continued)

Primary Examiner—Nikita Wells
(74) Attorney, Agent, or Firm—Diederiks & Whitelaw PLC (57) ABSTRACT

A mass spectrometer comprising an ion mobility separator for separating ions according to their ion mobility is disclosed. The ion mobility separator comprises a plurality of electrodes and one or more transient DC voltages or one or more transient DC voltage waveforms are progressively applied to the electrodes so that ions having a certain ion mobility are separated from other ions having different ion mobilities.

14 Claims, 7 Drawing Sheets

U.S. PATENT DOCUMENTS

| | | | |
|---|---|---|---|
| 5,140,158 A | 8/1992 | Post | |
| 5,206,506 A | 4/1993 | Kirchner | |
| 5,572,035 A | 11/1996 | Franzen | |
| 5,789,745 A | 8/1998 | Martin et al. | |
| 5,811,800 A | 9/1998 | Franzen et al. | |
| 5,818,055 A | 10/1998 | Franzen | |
| 5,847,386 A | 12/1998 | Thomson et al. | |
| 5,905,258 A | 5/1999 | Clemmer et al. | |
| 6,107,628 A | 8/2000 | Smith et al. | |
| 6,323,482 B1 | 11/2001 | Clemmer et al. | |
| 6,403,953 B2 | 6/2002 | Whitehouse et al. | |
| 6,417,511 B1 | 7/2002 | Russ, IV et al. | |
| 6,489,610 B1 | 12/2002 | Barofsky et al. | |
| 6,498,342 B1 | 12/2002 | Clemmer | |
| 6,545,268 B1 | 4/2003 | Verentchikov et al. | |
| 6,559,444 B2 | 5/2003 | Franzen | |
| 6,670,606 B2 | 12/2003 | Verentchikov et al. | |
| 6,690,004 B2 * | 2/2004 | Miller et al. | 250/286 |
| 6,693,276 B2 | 2/2004 | Weiss et al. | |
| 6,791,078 B2 * | 9/2004 | Giles et al. | 250/286 |
| 2001/0032929 A1 | 10/2001 | Fuhrer et al. | |
| 2002/0063207 A1 | 5/2002 | Bateman et al. | |
| 2002/0063209 A1 | 5/2002 | Bateman et al. | |
| 2002/0063210 A1 | 5/2002 | Bateman et al. | |
| 2002/0079443 A1 | 6/2002 | Krutchinsky et al. | |
| 2002/0113207 A1 | 8/2002 | Lee et al. | |
| 2002/0148959 A1 | 10/2002 | Weiss et al. | |
| 2002/0190200 A1 | 12/2002 | Zajfman et al. | |
| 2003/0001084 A1 * | 1/2003 | Bateman et al. | 250/281 |
| 2003/0201389 A1 * | 10/2003 | Hartley | 250/287 |

FOREIGN PATENT DOCUMENTS

| | | |
|---|---|---|
| GB | 2 382 919 A | 6/2003 |
| GB | 2 382 920 A | 6/2003 |
| JP | 11-307040 | 11/1999 |
| JP | 2000-113852 | 4/2000 |
| JP | 2000-123780 | 4/2000 |
| WO | WO 94/01883 | 1/1994 |
| WO | WO 94/28575 | 12/1994 |
| WO | WO 97/49111 | 12/1997 |
| WO | WO 98/56029 | 12/1998 |
| WO | WO 99/47912 | 9/1999 |
| WO | WO 00/70335 | 11/2000 |
| WO | WO 01/022049 | 3/2001 |
| WO | WO 02/43105 | 5/2002 |

OTHER PUBLICATIONS

Masuda et al., "Characteristics of Standing–Wave, Ring–Type Electric Curtain. Experimental Study", Electrical Engineering in Japan, vol. 93, No. 1, pp. 78–83, 1973.

Masuda et al., "Separation of Small Particles Suspended in Liquid by Nonuniform Traveling Field", IEEE Transactions on Industry Applications, vol. 1A–23, No. 3, pp. 474–480, 1987.

Masuda et al., "Approximation for Calculating Nonuniform Traveling Fields", Electrical Engineering In Japan, vol. 96, No. 5, pp. 25–31, 1976.

Gerlich, "Inhomogeneous RF Fields: A Versatile Tool For the Study of Processes With Slow Ions", Adv. In Chem. Phys. Ser., vol. 82, Ch. 1, pp. 1–176, 1992.

Teloy et al., "Integral Cross Sections For Ion–Molecule Reactions. I. The Guided Beam Technique", Chemical Physics, vol. 4, pp. 417–427, 1974.

Dodonov et al., "A New Technique For Decomposition of Selected Ions in Molecule Ion Reactor Coupled With Ortho–Time–Of–Flight Mass Spectrometry", Rapid Communications in Mass Spectrometry, vol. 11, pp. 1649–1656, 1997.

Shaffer et al., "A Novel Ion Funnel for Ion Focusing at Elevated Pressures", ASMS Book of Abstracts, pp. 375, 1997.

Gerlich et al., "Ion Trap Studies of Association Processes in Collisions of $CH_3^+$ and $CD_3^+$ With n–$H_2$, p–$H_2$, $D_2$, and He at 80 K", Astrophysical Journal, vol. 347, pp. 849–854, 1989.

Shaffer et al., "An Ion Funnel Interface for Improved Ion Focusing and Sensitivity Using Electrospray Ionization Mass Spectrometry", Analytical Chemistry, vol. 70, pp. 4111–4119, 1998.

Shaffer et al., "Characterization of an Improved Electrodynamic Ion Funnel Interface for Electrospray Ionization Mass Spectrometry", Analytical Chemistry, vol. 71, pp. 2957–2964, 1999.

Kim et al., "Design and Implementation of a New Electrodynamic Ion Funnel", Analytical Chemistry, vol. 72, pp. 2247–2255, 2000.

Tolmachev et al., "Charge Capacity Limitations of Radio Frequency Ion Guides in Their Use for Improved Ion Accumulation and Trapping in Mass Spectrometry". Analytical Chemistry, vol. 72, pp. 970–978, 2000.

Giles et al., "Evaluation of a Stacked–Ring Radio Frequency Ion Transmission Device at Intermediate Pressures", ASMS Book of Abstract, pp. 1, 2001.

Gerlich, "Rf Ion Guides", Encyclopedia of Mass Spectrometry, vol. 5, Chemistry and Physics of Gas–Phase Ions, pp. 1–34, 2003.

Luca et al., "On the Combination of a Linear Field Free Trap With a Time–Of Flight Mass Spectrometer", Review of Scientific Instruments, vol. 72, No. 7 pp. 2900–2908, 2001.

Guan et al., "Stacked–Ring Electrostatic Ion Guide", J. Am. Soc. Mass Spec., vol. 7, pp. 101–106, 1996.

Franzen, "Electrical Ion Guides", ASMS Book of Abstracts. pp. 1170, 1996.

Shaffer et al., "A Novel Ion Funnel For Focusing Ions at Elevated Pressure Using Electrospray Ionization Mass Spectrometry", Rapid Communications in Mass Spectrometry, vol. 11, pp. 1813–1917, 1997.

\* cited by examiner

MASS SPECTROMETER

CROSS-REFERENCE TO RELATED APPLICATIONS

The present application represents a continuation of U.S. patent application Ser. No. 10/603,824 filed Jun. 26, 2003 now U.S. Pat. No. 6,791,078 which claims the benefit of the filing date of U.S. Provisional Patent Application Ser. No. 60/422,134 filed Oct. 30, 2002.

BACKGROUND OF THE INVENTION

1. Field of the Invention

The present invention relates to a mass spectrometer, an ion mobility separator, a method of mass spectrometry and a method of ion mobility separation.

2. Discussion of the Prior Art

Radio Frequency (RF) ion guides are commonly used for confining and transporting ions. Conventionally a plurality of electrodes are provided wherein an RF voltage is applied between neighbouring electrodes so that a pseudo-potential well or valley is produced. The pseudo-potential well can be arranged to radially confine ions and may be used to efficiently transport ions by acting as an ion guide.

The RF ion guide is capable of functioning efficiently as an ion guide even at relatively high pressures wherein ions are likely to undergo frequent collisions with residual gas molecules. However, although the collisions with gas molecules may cause the ions to scatter and lose energy, the pseudo-potential well generated by the RF ion guide acts to radially confine the ions within the ion guide. RF ion guides therefore have an advantage over guide wire types of ion guides wherein a DC voltage is applied to a central wire running down the centre of a conducting tube. In such arrangements ions are held in orbit around the central guide wire and if ions undergo many collisions with gas molecules then they will tend to lose energy and will eventually collapse into the central guide wire and hence be lost. It is known to use RF ion guides to transport ions through vacuum chambers held at intermediate pressures (e.g. 0.001–10 mbar). For example, the ion guide may be provided to transmit ions from an atmospheric pressure source to a mass analyser in a chamber maintained at a relatively low pressure.

When ions collide with gas molecules they may get scattered and lose kinetic energy. If the ions undergo a large number of collisions, e.g. more than 100 collisions, then the ions will substantially lose all their forward kinetic energy. The ions will therefore possess a mean energy which is substantially equal to that of the surrounding gas molecules. The ions will therefore appear to move randomly within the gas due to continuing random collisions with gas molecules. Accordingly, under some operating conditions, ions being transported through an RF ion guide maintained at an intermediate gas pressure can lose substantially all their forward motion and may remain within the ion guide for a relatively long period of time.

In practice, ions may still continue to move forwards for other reasons. It is normally assumed that ions may continue to move forwards due to the bulk movement of gas forcing the ions through the ion guide. Space charge effects caused by the continual ingress of ions into the ion guide and hence the electrostatic repulsion from ions arriving from behind may also effectively push the ions through the ion guide. However, without these influences the ions can, in effect, come to a substantial standstill within the ion guide and hence not emerge at the exit.

A known means for driving ions through an RF ion guide at intermediate pressures is the use of a constant DC electric field. To ensure the ions emerge, or simply to reduce their transit time, an axial voltage gradient may be applied along the ion guide. For example, the ion guide may comprise a segmented multipole rod set ion guide with a DC potential maintained between successive rod segments. The axial electric field causes the ions to accelerate forwards after each collision with a gas molecule. A weak electric field, in the region of 0.1 to 1 V/cm, is adequate for pressures between 0.001 and 0.01 mbar. At higher pressures higher field strengths may be used.

In the pressure region above 0.001 mbar ions in an axial electric field will attain velocities according to their ion mobility. Ions emitted from a pulsed ion source can thus be arranged to separate according to their ion mobility. Ions from a continuous ion source may be gated into a drift region.

SUMMARY OF THE INVENTION

According to an aspect of the present invention there is provided a mass spectrometer comprising:

an ion mobility separator for separating ions according to their ion mobility, the ion mobility separator comprising a plurality of electrodes wherein in use one or more transient DC voltages or one or more transient DC voltage waveforms are progressively applied to the electrodes so that at least some ions having a first ion mobility are separated from other ions having a second different ion mobility.

According to a preferred embodiment a repeating pattern of electrical potentials are superimposed along the length of an ion mobility separator so as to form a periodic waveform. The waveform is caused to travel along the ion mobility separator in the direction in which it is required to move the ions and at the velocity at which it is required to move the ions.

The ion mobility separator may comprise an AC or RF ion guide such as a multipole rod set or a stacked ring set. The ion guide is preferably segmented in the axial direction so that independent transient DC potentials can be applied to each segment. The transient DC potentials are preferably superimposed on top of an AC or RF voltage which acts to radially confine ions and/or any constant DC offset voltage. The transient DC potentials generate a travelling wave which moves in the axial direction.

At any instant in time a voltage gradient is generated between segments which acts to push or pull ions in a certain direction. As the ions move in the required direction so does the voltage gradient. The individual DC voltages on each of the segments may be programmed to create a required waveform. The individual DC voltages on each of the segments may also be programmed to change in synchronism so that the DC potential waveform is maintained but is translated in the direction in which it is required to move the ions.

The one or more transient DC voltages or one or more transient DC voltage waveforms is preferably such that at least 10%, 20%, 30%, 40%, 50%, 60%, 70%, 80%, 90% or 95% of the ions having the first ion mobility are substantially moved along the ion mobility separator by the one or more transient DC voltages or the one or more transient DC voltage waveforms as the one or more transient DC voltage waveforms or the one or more transient DC voltage waveforms are progressively applied to the electrodes.

The one or more transient DC voltages or the one or more transient DC voltage waveforms are preferably such that at least 10%, 20%, 30%, 40%, 50%, 60%, 70%, 80%, 90% or 95% of the ions having the second ion mobility are moved along the ion mobility separator by the applied DC voltage to a lesser degree than the ions having the first ion mobility as the one or more transient DC voltages or the one or more transient DC voltage waveforms are progressively applied to the electrodes.

The one or more transient DC voltages or the one or more transient DC voltage waveforms are preferably such that at least 10%, 20%, 30%, 40%, 50%, 60%, 70%, 80%, 90% or 95% of the ions having the first ion mobility are moved along the ion mobility separator with a higher velocity than the ions having the second ion mobility.

According to another aspect of the present invention there is provided a mass spectrometer comprising:

an ion mobility separator for separating ions according to their ion mobility, the ion mobility separator comprising a plurality of electrodes wherein in use one or more transient DC voltages or one or more transient DC voltage waveforms are progressively applied to the electrodes so that ions are moved towards a region of the ion mobility separator wherein at least one electrode has a potential such that at least some ions having a first ion mobility will pass across the potential whereas other ions having a second different ion mobility will not pass across the potential.

The one or more transient DC voltages or the one or more transient DC voltage waveforms are preferably such that at least 10%, 20%, 30%, 40%, 50%, 60%, 70%, 80%, 90% or 95% of the ions having the first ion mobility pass across the potential. The one or more transient DC voltages or the one or more transient DC voltage waveforms are such that at least 10%, 20%, 30%, 40%, 50%, 60%, 70%, 80%, 90% or 95% of the ions having the second ion mobility will not pass across the potential. The at least one electrode is preferably provided with a voltage such that a potential hill or valley is provided.

The one or more transient DC voltages or the one or more transient DC voltage waveforms are preferably such that at least 10%, 20%, 30%, 40%, 50%, 60%, 70%, 80%, 90% or 95% of the ions having the first ion mobility exit the ion mobility separator substantially before ions having the second ion mobility. The one or more transient DC voltages or the one or more transient DC voltage waveforms are preferably such that at least 10%, 20%, 30%, 40%, 50%, 60%, 70%, 80%, 90% or 95% of the ions having the second ion mobility exit the ion mobility separator substantially after ions having the first ion mobility.

A majority of the ions having the first ion mobility preferably exit the ion mobility separator a time t before a majority of the ions having the second ion mobility exit the ion mobility separator, wherein t falls within a range selected from the group consisting of: (i) <1 $\mu$s; (ii) 1–10 $\mu$s; (iii) 10–50 $\mu$s; (iv) 50–100 $\mu$s; (v) 100–200 $\mu$s; (vi) 200–300 $\mu$s; (vii) 300–400 $\mu$s; (viii) 400–500 $\mu$s; (ix) 500–600 $\mu$s; (x) 600–700 $\mu$s; (xi) 700–800 $\mu$s; (xii) 800–900 $\mu$s; (xiii) 900–1000 $\mu$s; (xiv) 1.0–1.1 ms (xv) 1.1–1.2 ms; (xvi) 1.2–1.3 ms; (xvii) 1.3–1.4 ms; (xviii) 1.4–1.5 ms; (xix) 1.5–1.6 ms; (xx) 1.6–1.7 ms; (xxi) 1.7–1.8 ms; (xxii) 1.8–1.9 ms; (xxiii) 1.9–2.0 ms; (xxiv) 2.0–2.5 ms; (xxv) 2.5–3.0 ms; (xxvi) 3.0–3.5 ms; (xxvii) 3.5–4.0 ms; (xxviii) 4.0–4.5 ms; (xxix) 4.5–5.0 ms; (xxx) 5–10 ms; (xxxi) 10–15 ms; (xxxii) 15–20 ms; (xxxiii) 20–25 ms; and (xxxiv) 25–30 ms.

According to another aspect of the present invention there is provided a mass spectrometer comprising:

an ion mobility separator for separating ions according to their ion mobility, the ion mobility separator comprising a plurality of electrodes wherein in use one or more transient DC voltages or one or more transient DC voltage waveforms are progressively applied to the electrodes so that:

(i) ions are moved towards a region of the ion mobility separator wherein at least one electrode has a first potential such that at least some ions having first and second different ion mobilities will pass across the first potential whereas other ions having a third different ion mobility will not pass across the first potential; and then (ii) ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

The one or more transient DC voltages or the one or more transient DC voltage waveforms and the first potential are preferably such that at least 10%, 20%, 30%, 40%, 50%, 60%, 70%, 80%, 90% or 95% of the ions having the first ion mobility pass across the first potential. The one or more transient DC voltages or the one or more transient DC voltage waveforms and the first potential are preferably such that at least 10%, 20%, 30%, 40%, 50%, 60%, 70%, 80%, 90% or 95% of the ions having the second ion mobility pass across the first potential. The one or more transient DC voltages or the one or more transient DC voltage waveforms and the first potential are preferably such that at least 10%, 20%, 30%, 40%, 50%, 60%, 70%, 80%, 90% or 95% of the ions having the third ion mobility do not pass across the first potential.

The one or more transient DC voltages or the one or more transient DC voltage waveforms and the second potential are preferably such that at least 10%, 20%, 30%, 40%, 50%, 60%, 70%, 80%, 90% or 95% of the ions having the first ion mobility pass across the second potential. The one or more transient DC voltages or the one or more transient DC voltage waveforms and the second potential are preferably such that at least 10%, 20%, 30%, 40%, 50%, 60%, 70%, 80%, 90% or 95% of the ions having the second ion mobility do not pass across the second potential.

The one or more transient DC voltages or the one or more transient DC voltage waveforms are preferably such that at least 10%, 20%, 30%, 40%, 50%, 60%, 70%, 80%, 90% or 95% of the ions having the second ion mobility exit the ion mobility separator substantially before ions having the first and third ion mobilities. The one or more transient DC voltages or the one or more transient DC voltage waveforms are preferably such that at least 10%, 20%, 30%, 40%, 50%, 60%, 70%, 80%, 90% or 95% of the ions having the first and third ion mobilities exit the ion mobility separator substantially after ions having the second ion mobility.

A majority of the ions having the second ion mobility preferably exit the ion mobility separator a time t before a majority of the ions having the first and third ion mobilities exit the ion mobility separator, wherein t falls within a range selected from the group consisting of: (i) <1 $\mu$s; (ii) 1–10 $\mu$s; (iii) 10–50 $\mu$s; (iv) 50–100 $\mu$s; (v) 100–200 $\mu$s; (vi) 200–300 $\mu$s; (vii) 300–400 $\mu$s; (viii) 400–500 $\mu$s; (ix) 500–600 $\mu$s; (x) 600–700 $\mu$s; (xi) 700–800 $\mu$s; (xii) 800–900 $\mu$s; (xiii) 900–1000 $\mu$s; (xiv) 1.0–1.1 ms (xv) 1.1–1.2 ms; (xvi) 1.2–1.3 ms; (xvii) 1.3–1.4 ms; (xviii) 1.4–1.5 ms; (xix) 1.5–1.6 ms; (xx) 1.6–1.7 ms; (xxi) 1.7–1.8 ms; (xxii) 1.8–1.9 ms; (xxiii) 1.9–2.0 ms; (xxiv) 2.0–2.5 ms; (xxv) 2.5–3.0 ms; (xxvi) 3.0–3.5 ms; (xxvii) 3.5–4.0 ms; (xxviii) 4.0–4.5 ms; (xxix) 4.5–5.0 ms; (xxx) 5–10 ms; (xxxi) 10–15 ms; (xxxii) 15–20 ms; (xxxiii) 20–25 ms; and (xxxiv) 25–30 ms.

The one or more transient DC voltages may create: (i) a potential hill or barrier; (ii) a potential well; (iii) a combination of a potential hill or barrier and a potential well; (iv) multiple potential hills or barriers; (v) multiple potential wells; or (vi) a combination of multiple potential hills or barriers and multiple potential wells.

The one or more transient DC voltage waveforms preferably comprise a repeating waveform such as a square wave.

The one or more transient DC voltage waveforms preferably create a plurality of potential peaks or wells separated by intermediate regions. The DC voltage gradient in the intermediate regions is preferably non-zero and may be either positive or negative. The DC voltage gradient in the intermediate regions may be linear or non-linear. For example, the DC voltage gradient in the intermediate regions may increase or decrease exponentially.

The amplitude of the potential peaks or wells may remain substantially constant or the amplitude of the potential peaks or wells may become progressively larger or smaller. The amplitude of the potential peaks or wells may increase or decrease either linearly or non-linearly.

In use an axial DC voltage gradient is preferably maintained along at least a portion of the length of the ion mobility separator and wherein the axial voltage gradient varies with time.

The ion mobility separator may comprise a first electrode held at a first reference potential, a second electrode held at a second reference potential, and a third electrode held at a third reference potential, wherein: at a first time $t_1$ a first DC voltage is supplied to the first electrode so that the first electrode is held at a first potential above or below the first reference potential; at a second later time $t_2$ a second DC voltage is supplied to the second electrode so that the second electrode is held at a second potential above or below the second reference potential; and at a third later time $t_3$ a third DC voltage is supplied to the third electrode so that the third electrode is held at a third potential above or below the third reference potential.

Preferably, at the first time $t_1$ the second electrode is at the second reference potential and the third electrode is at the third reference potential; at the second time $t_2$ the first electrode is at the first potential and the third electrode is at the third reference potential; and at the third time $t_3$ the first electrode is at the first potential and the second electrode is at the second potential.

Alternatively, at the first time $t_1$ the second electrode is at the second reference potential and the third electrode is at the third reference potential; at the second time $t_2$ the first electrode is no longer supplied with the first DC voltage so that the first electrode is returned to the first reference potential and the third electrode is at the third reference potential; and at the third time $t_3$ the first electrode is at the first reference potential the second electrode is no longer supplied with the second DC voltage so that the second electrode is returned to the second reference potential.

The first, second and third reference potentials are preferably substantially the same. Preferably, the first, second and third DC voltages are substantially the same. Preferably, the first, second and third potentials are substantially the same.

The ion mobility separator may comprise 3, 4, 5, 6, 7, 8, 9, 10, 11, 12, 13, 14, 15, 16, 17, 18, 19, 20, 21, 22, 23, 24, 25, 26, 27, 28, 29, 30 or >30 segments, wherein each segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or >30 electrodes and wherein the electrodes in a segment are maintained at substantially the same DC potential. Preferably, a plurality of segments are maintained at substantially the same DC potential. Preferably, each segment is maintained at substantially the same DC potential as the subsequent nth segment wherein n is 3, 4, 5, 6, 7, 8, 9, 10, 11, 12, 13, 14, 15, 16, 17, 18, 19, 20, 21, 22, 23, 24, 25, 26, 27, 28, 29, 30 or >30.

Ions are preferably confined radially within the ion mobility separator by an AC or RF electric field. Ions are preferably radially confined within the ion mobility separator in a pseudo-potential well and are moved axially by a real potential barrier or well.

In use one or more additional AC or RF voltage waveforms may be applied to at least some of the electrodes so that ions are urged along at least a portion of the length of the ion mobility separator. Such AC or RF voltage waveforms are additional to the AC or RF voltages which radially confine ions within the ion mobility separator.

The transit time of ions through the ion mobility separator is preferably selected from the group consisting of: (i) less than or equal to 20 ms; (ii) less than or equal to 10 ms; (iii) less than or equal to 5 ms; (iv) less than or equal to 1 ms; and (v) less than or equal to 0.5 ms.

The ion mobility separator may be maintained in use at a pressure selected from the group consisting of: (i) greater than or equal to 0.0001 mbar; (ii) greater than or equal to 0.0005 mbar; (iii) greater than or equal to 0.001 mbar; (iv) greater than or equal to 0.005 mbar; (v) greater than or equal to 0.01 mbar; (vi) greater than or equal to 0.05 mbar; (vii) greater than or equal to 0.1 mbar; (viii) greater than or equal to 0.5 mbar; (ix) greater than or equal to 1 mbar; (x) greater than or equal to 5 mbar; and (xi) greater than or equal to 10 mbar. Preferably, the ion mobility separator is maintained in use at a pressure selected from the group consisting of: (i) less than or equal to 10 mbar; (ii) less than or equal to 5 mbar; (iii) less than or equal to 1 mbar; (iv) less than or equal to 0.5 mbar; (v) less than or equal to 0.1 mbar; (vi) less than or equal to 0.05 mbar; (vii) less than or equal to 0.01 mbar; (viii) less than or equal to 0.005 mbar; (ix) less than or equal to 0.001 mbar; (x) less than or equal to 0.0005 mbar; and (xi) less than or equal to 0.0001 mbar. Preferably, the ion mobility separator is maintained, in use, at a pressure selected from the group consisting of: (i) between 0.0001 and 10 mbar; (ii) between 0.0001 and 1 mbar; (iii) between 0.0001 and 0.1 mbar; (iv) between 0.0001 and 0.01 mbar; (v) between 0.0001 and 0.001 mbar; (vi) between 0.001 and 10 mbar; (vii) between 0.001 and 1 mbar; (viii) between 0.001 and 0.1 mbar; (ix) between 0.001 and 0.01 mbar; (x) between 0.01 and 10 mbar; (xi) between 0.01 and 1 mbar; (xii) between 0.01 and 0.1 mbar; (xiii) between 0.1 and 10 mbar; (xiv) between 0.1 and 1 mbar; and (xv) between 1 and 10 mbar.

The ion mobility separator is preferably maintained, in use, at a pressure such that a viscous drag is imposed upon ions passing through the ion mobility separator.

In use the one or more transient DC voltages or the one or more transient DC voltage waveforms are preferably initially provided at a first axial position and are then subsequently provided at second, then third different axial positions along the ion mobility separator.

The one or more transient DC voltages or the one or more transient DC voltage waveforms preferably move from one end of the ion mobility separator to another end of the ion mobility separator so that at least some ions are urged along the ion mobility separator.

The one or more transient DC voltages or the one or more transient DC voltage waveforms preferably have at least 2, 3, 4, 5, 6, 7, 8, 9 or 10 different amplitudes.

The amplitude of the one or more transient DC voltages or the one or more transient DC voltage waveforms may remain substantially constant with time or alternatively the amplitude of the one or more transient DC voltages or the one or more transient DC voltage waveforms may vary with time. For example, the amplitude of the one or more transient DC voltages or the one or more transient DC voltage waveforms either: (i) increases with time; (ii) increases then decreases with time; (iii) decreases with time; or (iv) decreases then increases with time.

The ion mobility separator may comprise an upstream entrance region, a downstream exit region and an intermediate region, wherein: in the entrance region the amplitude of the one or more transient DC voltages or the one or more transient DC voltage waveforms has a first amplitude; in the intermediate region the amplitude of the one or more transient DC voltages or the one or more transient DC voltage waveforms has a second amplitude; and in the exit region the amplitude of the one or more transient DC voltages or the one or more transient DC voltage waveforms has a third amplitude.

The entrance and/or exit region preferably comprise a proportion of the total axial length of the ion mobility separator selected from the group consisting of: (i) <5%; (ii) 5–10%; (iii) 10–15%; (iv) 15–20%; (v) 20–25%; (vi) 25–30%; (vii) 30–35%; (viii) 35–40%; and (ix) 40–45%.

The first and/or third amplitudes are preferably substantially zero and the second amplitude is substantially non-zero. Preferably, the second amplitude is larger than the first amplitude and/or the second amplitude is larger than the third amplitude.

The one or more transient DC voltages or the one or more transient DC voltage waveforms preferably pass in use along the ion mobility separator with a first velocity. Preferably, the first velocity: (i) remains substantially constant; (ii) varies; (iii) increases; (iv) increases then decreases; (v) decreases; (vi) decreases then increases; (vii) reduces to substantially zero; (viii) reverses direction; or (ix) reduces to substantially zero and then reverses direction.

The one or more transient DC voltages or the one or more transient DC voltage waveforms preferably cause some ions within the ion mobility separator to pass along the ion mobility separator with a second different velocity. Preferably, the one or more transient DC voltages or the one or more transient DC voltage waveforms causes some ions within the ion mobility separator to pass along the ion mobility separator with a third different velocity. Preferably, the one or more transient DC voltages or the one or more transient DC voltage waveforms causes some ions within the ion mobility separator to pass along the ion mobility separator with a fourth different velocity. Preferably, the one or more transient DC voltages or the one or more transient DC voltage waveforms causes some ions within the ion mobility separator to pass along the ion mobility separator with a fifth different velocity.

The difference between the first velocity and the second and/or the third and/or the fourth and/or the fifth velocities is preferably selected from the group consisting of: (i) less than or equal to 50 m/s; (ii) less than or equal to 40 m/s; (iii) less than or equal to 30 m/s; (iv) less than or equal to 20 m/s; (v) less than or equal to 10 m/s; (vi) less than or equal to 5 m/s; and (vii) less than or equal to 1 m/s;

The first velocity is preferably selected from the group consisting of: (i) 10–250 m/s; (ii) 250–500 m/s; (iii) 500–750 m/s; (iv) 750–1000 m/s; (v) 1000–1250 m/s; (vi) 1250–1500 m/s; (vii) 1500–1750 m/s; (viii) 1750–2000 m/s; (ix) 2000–2250 m/s; (x) 2250–2500 m/s; (xi) 2500–2750 m/s; and (xii) 2750–3000 m/s. The second and/or the third and/or the fourth and/or the fifth different velocity is preferably selected from the group consisting of: (i) 10–250 m/s; (ii) 250–500 m/s; (iii) 500–750 m/s; (iv) 750–1000 m/s; (v) 1000–1250 m/s; (vi) 1250–1500 m/s; (vii) 1500–1750 m/s; (viii) 1750–2000 m/s; (ix) 2000–2250 m/s; (x) 2250–2500 m/s; (xi) 2500–2750 m/s; and (xii) 2750–3000 m/s.

The one or more transient DC voltages or the one or more transient DC voltage waveforms preferably has a frequency, and wherein the frequency: (i) remains substantially constant; (ii) varies; (iii) increases; (iv) increases then decreases; (v) decreases; or (vi) decreases then increases.

The one or more transient DC voltages or the one or more transient DC voltage waveforms preferably has a wavelength, and wherein the wavelength: (i) remains substantially constant; (ii) varies; (iii) increases; (iv) increases then decreases; (v) decreases; or (vi) decreases then increases.

Two or more transient DC voltages or two or more transient DC voltage waveforms may pass simultaneously along the ion mobility separator. The two or more transient DC voltages or the two or more transient DC voltage waveforms may be arranged to move: (i) in the same direction; (ii) in opposite directions; (iii) towards each other; or (iv) away from each other.

The one or more transient DC voltages or the one or more transient DC voltage waveforms may pass along the ion mobility separator and at least one substantially stationary transient DC potential voltage or voltage waveform is provided at a position along the ion mobility separator.

The one or more transient DC voltages or the one or more transient DC voltage waveforms are preferably repeatedly generated and passed in use along the ion mobility separator, and wherein the frequency of generating the one or more transient DC voltages or the one or more transient DC voltage waveforms: (i) remains substantially constant; (ii) varies; (iii) increases; (iv) increases then decreases; (v) decreases; or (vi) decreases then increases.

A continuous beam of ions may be received at an entrance to the ion mobility separator or packets of ions may be received at an entrance to the ion mobility separator.

Pulses of ions preferably emerge from an exit of the ion mobility separator. The mass spectrometer preferably further comprises an ion detector, the ion detector being arranged to be substantially phase locked in use with the pulses of ions emerging from the exit of the ion mobility separator. The mass spectrometer also preferably further comprises a Time of Flight mass analyser comprising an electrode for injecting ions into a drift region, the electrode being arranged to be energised in use in a substantially synchronised manner with the pulses of ions emerging from the exit of the ion mobility separator.

The ion mobility separator is preferably selected from the group consisting of: (i) an ion funnel comprising a plurality of electrodes having apertures therein through which ions are transmitted, wherein the diameter of the apertures becomes progressively smaller or larger; (ii) an ion tunnel comprising a plurality of electrodes having apertures therein through which ions are transmitted, wherein the diameter of the apertures remains substantially constant; and (iii) a stack of plate, ring or wire loop electrodes.

The ion mobility separator preferably comprises a plurality of electrodes, each electrode having an aperture through which ions are transmitted in use. Each electrode may have a substantially circular aperture. Each electrode may have a single aperture through which ions are transmitted in use.

The diameter of the apertures of at least 10%, 20%, 30%, 40%, 50%, 60%, 70%, 80%, 90% or 95% of the electrodes forming the ion mobility separator is preferably selected from the group consisting of: (i) less than or equal to 10 mm; (ii) less than or equal to 9 mm; (iii) less than or equal to 8 mm; (iv) less than or equal to 7 mm; (v) less than or equal to 6 mm; (vi) less than or equal to 5 mm; (vii) less than or equal to 4 mm; (viii) less than or equal to 3 mm; (ix) less than or equal to 2 mm; and (x) less than or equal to 1 mm.

At least 10%, 20%, 30%, 40%, 50%, 60%, 70%, 80%, 90% or 95% of the electrodes forming the ion mobility separator preferably have apertures which are substantially the same size or area.

According to a less preferred embodiment the ion mobility separator may comprise a segmented rod set.

The ion mobility separator preferably consists of: (i) 10–20 electrodes; (ii) 20–30 electrodes; (iii) 30–40 electrodes; (iv) 40–50 electrodes; (v) 50–60 electrodes; (vi) 60–70 electrodes; (vii) 70–80 electrodes; (viii) 80–90 electrodes; (ix) 90–100 electrodes; (x) 100–110 electrodes; (xi) 110–120 electrodes; (xii) 120–130 electrodes; (xiii) 130–140 electrodes; (xiv) 140–150 electrodes; or (xv) more than 150 electrodes.

The thickness of at least 10%, 20%, 30%, 40%, 50%, 60%, 70%, 80%, 90% or 95% of the electrodes is preferably selected from the group consisting of: (i) less than or equal to 3 mm; (ii) less than or equal to 2.5 mm; (iii) less than or equal to 2.0 mm; (iv) less than or equal to 1.5 mm; (v) less than or equal to 1.0 mm; and (vi) less than or equal to 0.5 mm.

The ion mobility separator preferably has a length selected from the group consisting of: (i) less than 5 cm; (ii) 5–10 cm; (iii) 10–15 cm; (iv) 15–20 cm; (v) 20–25 cm; (vi) 25–30 cm; and (vii) greater than 30 cm.

At least 10%, 20%, 30%, 40%, 50%, 60%, 70%, 80%, 90%, or 95% of the electrodes are preferably connected to both a DC and an AC or RF voltage supply. According to the preferred embodiment axially adjacent electrodes are supplied with AC or RF voltages having a phase difference of 180°.

The mass spectrometer may comprise an ion source selected from the group consisting of: (i) Electrospray ("ESI") ion source; (ii) Atmospheric Pressure Chemical Ionisation ("APCI") ion source; (iii) Atmospheric Pressure Photo Ionisation ("APPI") ion source; (iv) Matrix Assisted Laser Desorption Ionisation ("MALDI") ion source; (v) Laser Desorption Ionisation ("LDI") ion source; (vi) Inductively Coupled Plasma ("ICP") ion source; (vii) Electron Impact ("EI") ion source; (viii) Chemical Ionisation ("CI") ion source; (ix) a Fast Atom Bombardment ("FAB") ion source; and (x) a Liquid Secondary Ions Mass Spectrometry ("LSIMS") ion source. The ion source may be either a continuous or a pulsed ion source.

According to another aspect of the present invention, there is provided an ion mobility separator for separating ions according to their ion mobility, the ion mobility separator comprising a plurality of electrodes wherein in use one or more transient DC voltages or one or more transient DC voltage waveforms are progressively applied to the electrodes so that at least some ions having a first ion mobility are separated from other ions having a second different ion mobility.

According to another aspect of the present invention, there is provided an ion mobility separator for separating ions according to their ion mobility, the ion mobility separator comprising a plurality of electrodes wherein in use one or more transient DC voltages or one or more transient DC voltage waveforms are progressively applied to the electrodes so that ions are moved towards a region of the ion mobility separator wherein at least one electrode has a potential such that at least some ions having a first ion mobility will pass across the potential whereas other ions having a second different ion mobility will not pass across the potential.

According to another aspect of the present invention, there is provided an ion mobility separator for separating ions according to their ion mobility, the ion mobility separator comprising a plurality of electrodes wherein in use one or more transient DC voltages or one or more transient DC voltage waveforms are progressively applied to the electrodes so that:

(i) ions are moved towards a region of the ion mobility separator wherein at least one electrode has a first potential such that at least some ions having first and second different ion mobilities will pass across the first potential whereas other ions having a third different ion mobility will not pass across the first potential; and then (ii) ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

According to another aspect of the present invention, there is provided a method of mass spectrometry comprising:

receiving ions in an ion mobility separator comprising a plurality of electrodes; and progressively applying to the electrodes one or more transient DC voltages or one or more transient DC voltage waveforms so that at least some ions having a first ion mobility are separated from other ions having a second different ion mobility.

According to another aspect of the present invention, there is provided a method of mass spectrometry comprising:

receiving ions in an ion mobility separator comprising a plurality of electrodes; and progressively applying to the electrodes one or more transient DC voltages or one or more transient DC voltage waveforms so that ions are moved towards a region of the ion mobility separator wherein at least one electrode has a potential such that at least some ions having a first ion mobility will pass across the potential whereas other ions having a second different ion mobility will not pass across the potential.

According to another aspect of the present invention, there is provided a method of mass spectrometry comprising:

receiving ions in an ion mobility separator comprising a plurality of electrodes;

progressively applying to the electrodes one or more transient DC voltages or one or more transient DC voltage waveforms so that ions are moved towards a region of the ion mobility separator wherein at least one electrode has a first potential such that at least some ions having a first and second different ion mobilities will pass across the first potential whereas other ions having a third different ion mobility will not pass across the first potential; and then progressively applying to the electrodes one or more transient DC voltages or one or more transient DC voltage waveforms so that ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

According to another aspect of the present invention, there is provided a method of ion mobility separation comprising:

receiving ions in an ion mobility separator comprising a plurality of electrodes; and progressively applying to the electrodes one or more transient DC voltages or one or more transient DC voltage waveforms so that at least some ions having a first ion mobility are separated from other ions having a second different ion mobility.

According to another aspect of the present invention, there is provided a method of ion mobility separation comprising:

receiving ions in an ion mobility separator is comprising a plurality of electrodes; and progressively applying to the electrodes one or more transient DC voltages or one or more transient DC voltage waveforms so that ions are moved towards a region of the ion mobility separator wherein at least one electrode has a potential such that at least some ions having a first ion mobility will pass across the potential whereas other ions having a second different ion mobility will not pass across the potential.

According to another aspect of the present invention, there is provided a method of ion mobility separation comprising:

receiving ions in an ion mobility separator comprising a plurality of electrodes;

progressively applying to the electrodes one or more transient DC voltages or one or more transient DC voltage waveforms so that ions are moved towards a region of the ion mobility separator wherein at least one electrode has a first potential such that at least some ions having a first and second different ion mobilities will pass across the first potential whereas other ions having a third different ion mobility will not pass across the first potential; and then progressively applying to the electrodes one or more transient DC voltages or one or more transient DC voltage waveforms so that ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

According to another aspect of the present invention, there is provided an ion mobility separator wherein ions separate within the ion mobility separator according to their ion mobility and assume different essentially static or equilibrium axial positions along the length of the ion mobility separator.

The ion mobility separator preferably comprises a plurality of electrodes and wherein one or more transient DC voltages or one or more transient DC voltage waveforms are progressively applied to the electrodes so as to urge at least some ions in a first direction and wherein a DC voltage gradient acts to urge at least some ions in a second direction, the second direction being opposed to the first direction.

The peak amplitude of the one or more transient DC voltages or the one or more transient DC voltage waveforms preferably remains substantially constant or reduces along the length of the ion mobility separator.

The DC voltage gradient preferably progressively increases along the length of the ion mobility separator.

Once ions have assumed essentially static or equilibrium axial positions along the length of the ion mobility separator at least some of the ions may then be arranged to be moved towards an exit of the ion mobility separator. At least some of the ions may be arranged to be moved towards an exit of the ion mobility separator by: (i) reducing or increasing an axial DC voltage gradient; (ii) reducing or increasing the peak amplitude of the one or more transient DC voltages or the one or more transient DC voltage waveforms; (iii) reducing or increasing the velocity of the one or more transient DC voltages or the one or more transient DC voltage waveforms; or (iv) reducing or increasing the pressure within the ion mobility separator.

According to another aspect of the present invention, there is provided a mass spectrometer comprising an ion mobility separator as described above.

According to another aspect of the present invention, there is provided a method of ion mobility separation comprising causing ions to separate within an ion mobility separator and assume different essentially static or equilibrium axial positions along the length of the ion mobility separator.

The ion mobility separator may comprise a plurality of electrodes and wherein one or more transient DC voltages or one or more transient DC voltage waveforms are progressively applied to the electrodes so as to urge at least some ions in a first direction and wherein a DC voltage gradient acts to urge at least some ions in a second direction, the second direction being opposed to the first direction.

According to another aspect of the present invention, there is provided a method of mass spectrometry comprising:

providing an ion mobility separator for separating ions according to their ion mobility, the ion mobility separator comprising a plurality of electrodes wherein in use one or more transient DC voltages or one or more transient DC voltage waveforms are progressively applied to the electrodes so that at least some ions having a first ion mobility are separated from other ions having a second different ion mobility;

separating ions according to their ion mobility in the ion mobility separator;

providing a quadrupole mass filter downstream of the ion mobility separator; and scanning the quadrupole mass filter in a stepped manner in synchronisation with the ion mobility separator so as to onwardly transmit ions having a desired charge state.

According to another aspect of the present invention, there is provided a mass spectrometer comprising:

an ion mobility separator for separating ions according to their ion mobility, the ion mobility separator comprising a plurality of electrodes wherein in use one or more transient DC voltages or one or more transient DC voltage waveforms are progressively applied to the electrodes so that at least some ions having a first ion mobility are separated from other ions having a second different ion mobility; and a quadrupole mass filter downstream of the ion mobility separator;

wherein the quadrupole mass filter is scanned in use in a stepped manner in synchronisation with the ion mobility separator so as to onwardly transmit ions having a desired charge state.

BRIEF DESCRIPTION OF THE DRAWINGS

Various embodiment of the present invention will now be described, by way of example only, and with reference to the accompanying drawings in which.

DETAILED DESCRIPTION OF THE PREFERRED EMBODIMENTS

Figure 1:
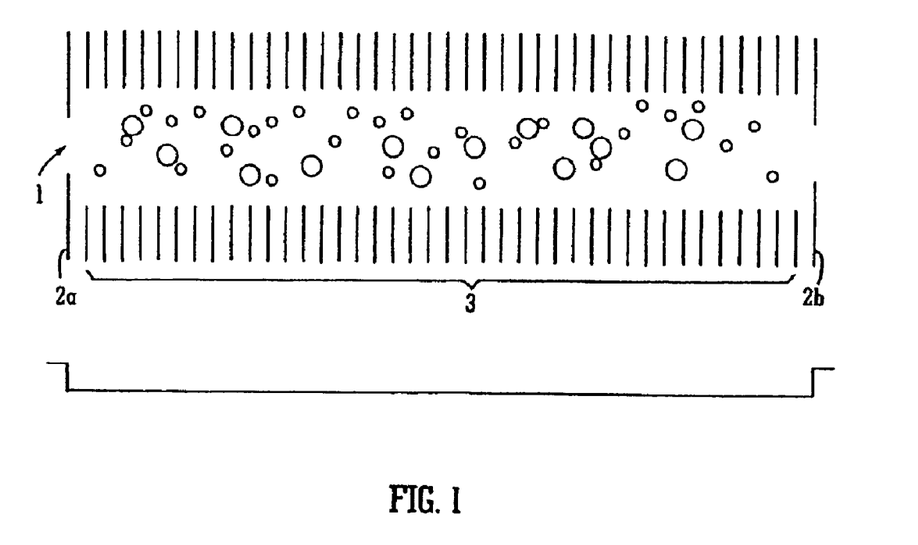
FIG. 1 shows equilibrium in a preferred ion mobility separator together with the voltage profile along the length of the ion mobility separator.
Figure 2:
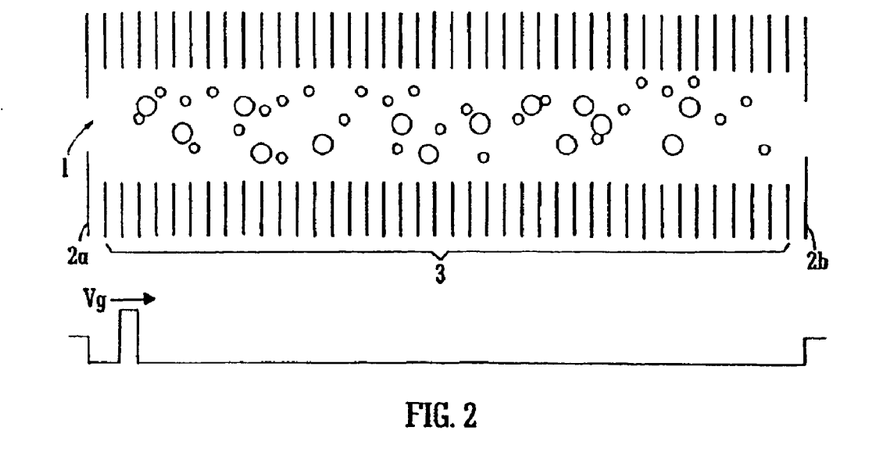
FIG. 2 shows ions within an ion mobility separator as a travelling DC voltage begins at one end of the preferred ion mobility separator together with the voltage profile along the length of the ion mobility separator.

FIG. 1 shows a preferred ion mobility separator 1 comprising a plurality of electrodes 3 each having an aperture through which ions may be transmitted. Adjacent electrodes 3 are preferably connected to opposite phases of an AC or RF voltage supply. The ion mobility separator 1 is preferably held at a pressure such that ions traversing its length undergo many collisions with gas molecules. The ion mobility separator 1 may according to one embodiment receive ions generated by an Electrospray or a MALDI ion source. One or more end plates 2a,2b of the ion mobility separator 1 may be maintained at a slight positive voltage relative to the other electrodes 3 so that ions once entering the ion mobility separator 1 are effectively trapped within the ion mobility separator 1 and are unable to surmount the potential barrier at one or both ends. After a certain period of time equilibrium may be reached within the ion mobility separator 1 so that ions of all masses and mobilities are substantially equally distributed along the length of the ion mobility separator 1. As shown in FIG. 2, according to one embodiment a voltage pulse Vg may be applied to the first electrode of the ion guide adjacent to one of the end plates 2a so that some ions will be pushed by the applied voltage pulse Vg along the ion mobility separator 1. The local field variation is given by:

$$V_{drift} = KE(x)$$

where $V_{drift}$ is the drift velocity of an ion, K is the mobility of the ion and E(x) is the electric field caused by the applied voltage. The electric field caused by the applied voltage decays rapidly to a negligible value within a few electrode spacings.

The voltage pulse Vg is then preferably rapidly switched to the next adjacent electrode. An ion which has had enough time to drift at least one electrode spacing will therefore experience the same force and will again move along the length of the ion mobility separator 1 in the direction in which the voltage pulse Vg is heading. However, ions having a lower ion mobility may not have had sufficient time to drift far enough to see the influence of the voltage when it switched to the adjacent electrode. Accordingly, these lower mobility ions will be effectively left behind by the travelling voltage pulse Vg or voltage waveform.

Figure 3:
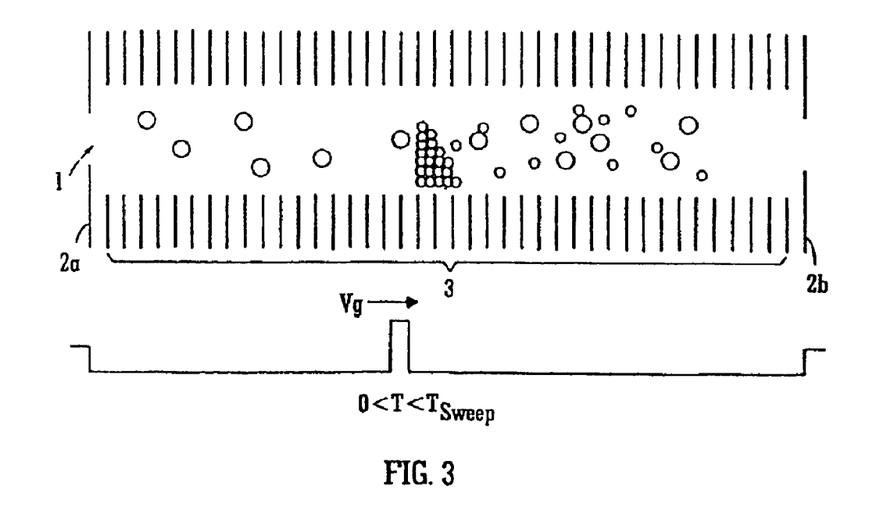
FIG. 3 shows the effect as a travelling DC voltage wave sweeps high mobility ions towards one end of the preferred ion mobility separator together with the voltage profile along the length of the ion mobility separator.
Figure 4:
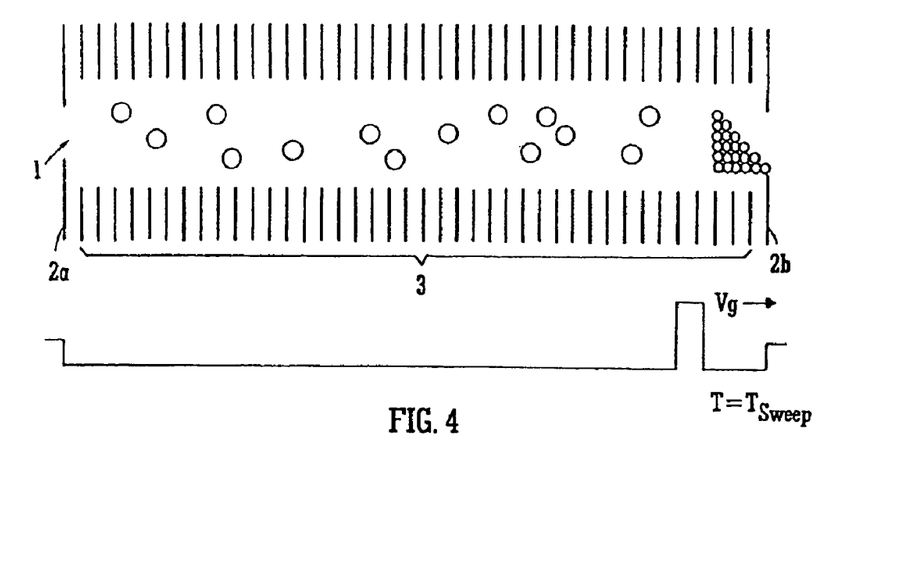
FIG. 4 shows an embodiment wherein all high mobility ions have been swept towards one end of the preferred ion mobility separator and the ions are then ejected from the preferred ion mobility separator together with the voltage profile along the ion mobility separator.

The voltage pulse Vg preferably travels along the ion mobility separator 1 from electrode to electrode sweeping those ions with a sufficiently high ion mobility with it. As shown in FIGS. 3 and 4 the ion mobility separator 1 may therefore in one embodiment act as a high pass ion mobility filter such that ions having ion mobilities greater than a certain value are preferably ejected from the ion mobility separator 1 whereas ions having lower ion mobilities remain substantially trapped within the ion mobility separator 1.

The sweep time $T_{sweep}$ of the ion mobility separator 1 may then be reduced to select a slightly lower (intermediate) ion mobility so that those ions having an intermediate ion mobility may then be subsequently ejected from the ion mobility separator 1. By gradually further reducing the sweep time a complete mobility scan may be built up until the ion mobility separator 1 is substantially empty of ions.

According to another mode of operation the voltage of the voltage pulse Vg may be progressively increased with each sweep thereby collecting ions having progressively decreasing ion mobilities in the same way. It will be appreciated from consideration of the above equation that doubling the voltage will double the velocity of an ion.

The resolution of the ion mobility separator 1 will in part be determined by the sweep time $T_{sweep}$ or voltage increment. The smaller the step (i.e. reduction in sweep time or increase in the voltage of the voltage pulse) between the adjacent sweeps the greater the resolution of the ion mobility separator 1. FIG. 4 shows ions at the end of a voltage sweep being ejected from the ion mobility separator 1.

Figure 5:
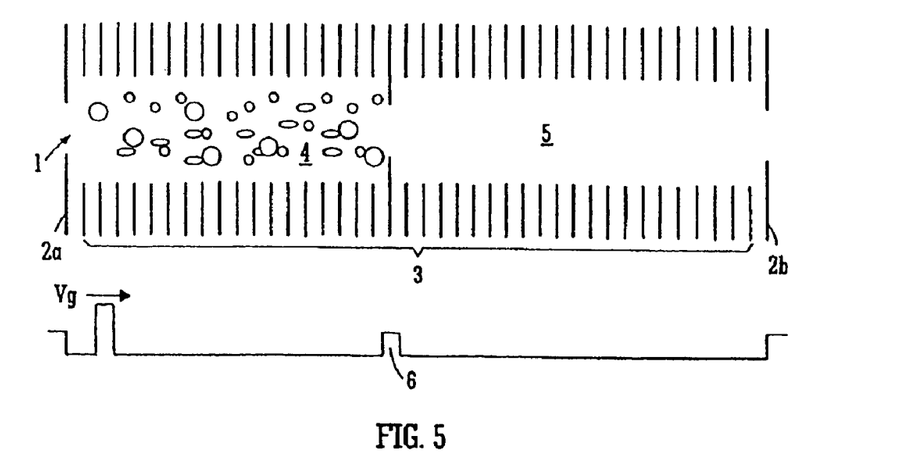
FIG. 5 shows at equilibrium another embodiment wherein the preferred ion mobility separator is divided into two regions separated by a potential hill together with the voltage profile along the length of the ion mobility separator.
Figure 6:
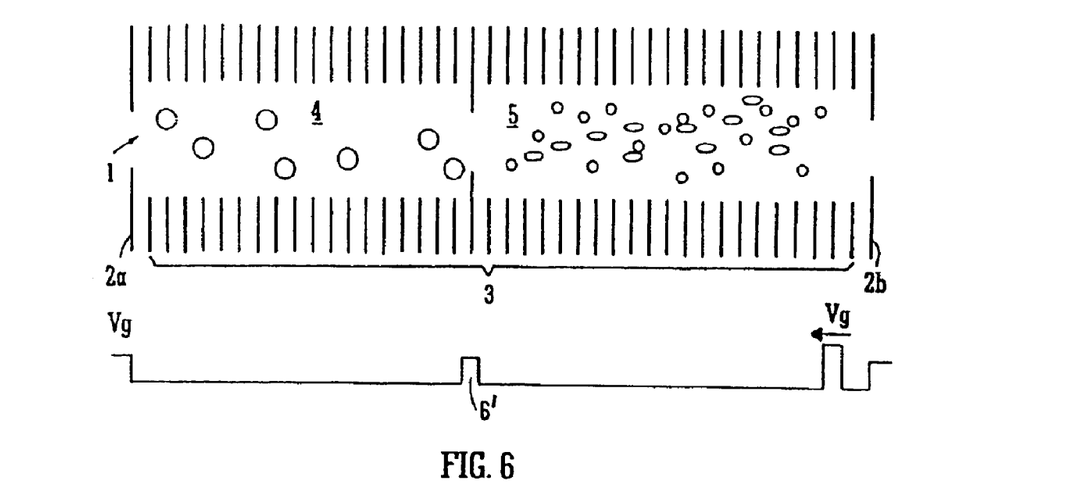
FIG. 6 shows an embodiment wherein higher mobility ions have been swept into a second region of the ion mobility separator and wherein a travelling DC voltage wave reverses in direction together with the voltage profile along the length of the ion mobility separator.
Figure 7:
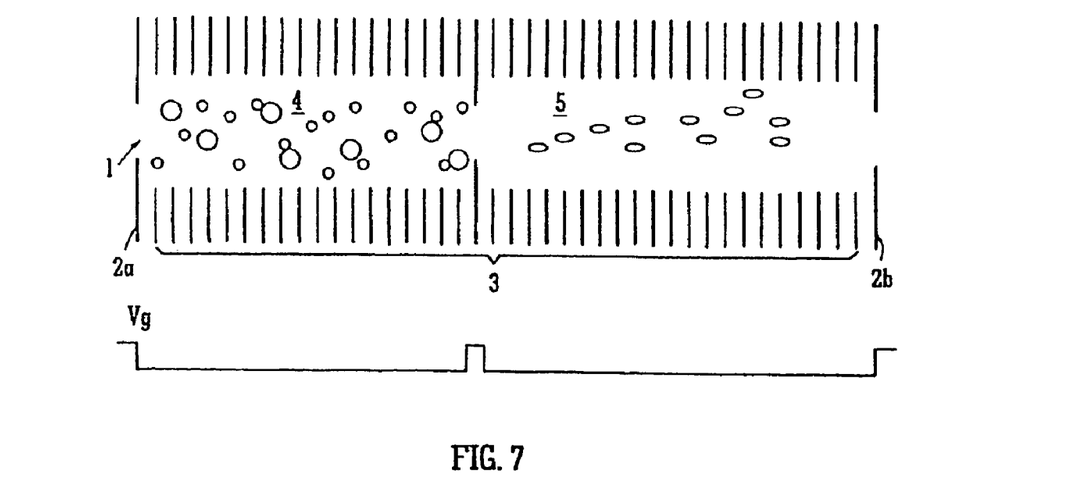
FIG. 7 shows a bandpass mode of operation embodiment wherein ions having an intermediate ion mobility are left in a second stage of the preferred ion mobility separator together with the voltage profile along the length of the ion mobility separator.

The mode of operation described above may build up a mobility spectrum by a series of high pass further steps. However, isolation of a particular range of ion mobilities i.e. bandpass operation may also be achieved by employing a two stage device. As shown in FIG. 5, ions with an ion mobility greater than a certain value may be arranged to pass along a portion of the ion mobility separator 1 by the operation of a voltage pulse Vg passing along the ion mobility separator 1. The ions then pass from a first region 4 to an electrode which is maintained at a certain potential 6 and into a second region 5 which is preferably substantially empty of ions. As shown in FIG. 6, once some ions have been swept into the second region 5 the travelling voltage pulse Vg may then be reversed so as to sweep some ions from the second region 5 past the same (or another electrode) which is maintained at a preferably lower potential 6' back into the first region 4. The reverse sweep may be faster and/or have a higher voltage than the forward sweep so that as shown in FIG. 7 ions having ion mobilities within a desired range may remain trapped in the second region 5.

The resolution of the ion mobility separator 1 has been modelled to include the effect of diffusion of ions. Diffusion effects are known to degrade the resolution of conventional drift tube ion mobility separators and the relationship between the drift tube length and the applied axial voltage drop is given by:

$$\frac{|X|}{L} = \frac{0.173}{\sqrt{V}}$$

where mod X is the spatial spread due to diffusion, L is the length of the drift tube and V the applied axial voltage drop.

To increase the resolving power of a conventional mobility spectrometer longer drift tubes and higher voltages may be employed. However, an advantage of the preferred ion mobility separator 1 is that the voltage required can be a relatively low e.g. 10V at a pressure of 2 mbar. Furthermore, the low (10V) voltage only needs to be applied to a single electrode at any one point in time. The preferred ion mobility separator 1 can therefore achieve ion mobility separation using a low voltage source whereas a conventional drift tube type ion mobility spectrometer would require approximately 1000V to achieve comparable ion mobility separation.

Figure 8:
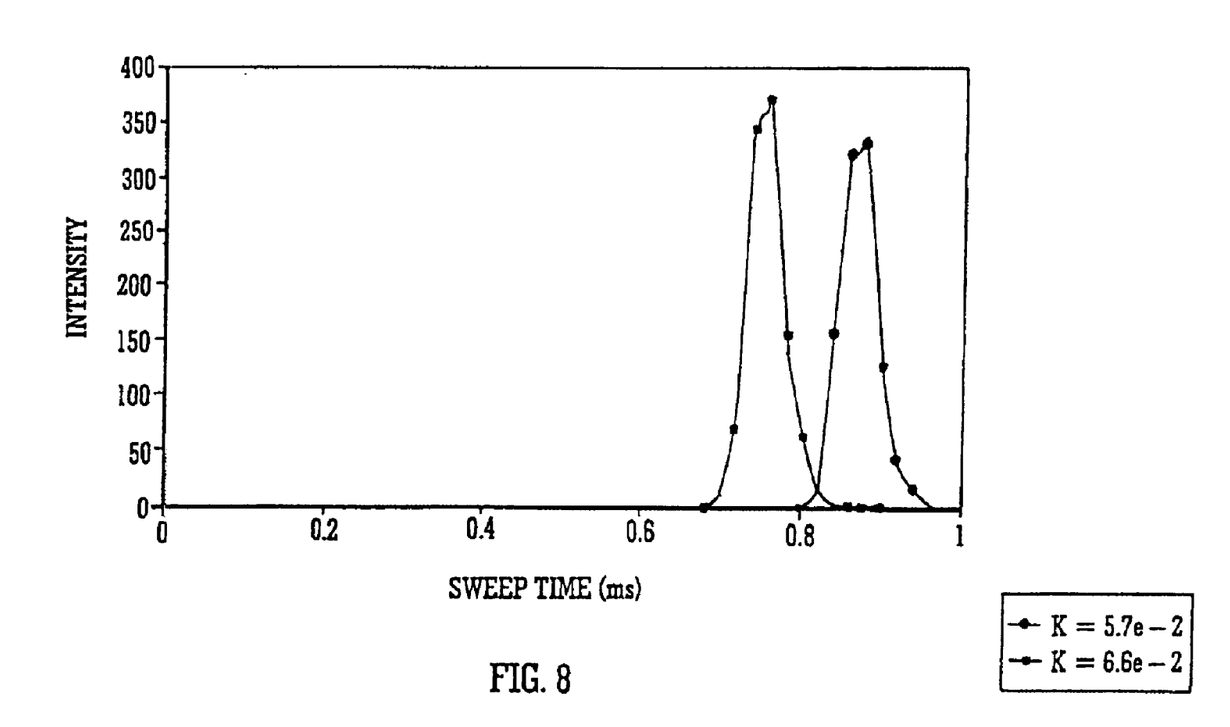
FIG. 8 shows a predetermined separation of two samples.

The ion mobility separator 1 has been modelled as a series of electrodes with a voltage resident on each electrode for a certain period of time. Diffusion was introduced into the model as a random scattering component over the time of residence of the voltage on an element. The result of this simulation is shown in FIG. 8 and predicts the complete separation of Gramacidin S (m/z 572) and Leucine Enkephalin (m/z 556). The model was based on an ion mobility separator 1 having 100 electrodes and wherein a voltage of 7V was progressively applied along the length of the ion mobility separator 1. This result is comparable with the performance which may be expected from a conventional drift tube ion mobility separator of similar dimensions Further improvements in resolution may be achieved by sweeping the ions backwards and forwards through the same volume a number of times. This has the effect of increasing the effective length of the ion mobility separator 1 without actually increasing its physical dimensions. A more compact ion mobility separator than a conventional ion mobility spectrometer may therefore be provided according to a preferred embodiment. As will be appreciated, a greater number of passes through the ion mobility separator 1 allows for greater isolation of the desired species of ions.

Ions may be purged from the swept volume after the passage of the travelling voltage wave by switching the AC or RF voltage OFF and allowing ions to diffuse out of that portion of the ion mobility separator 1. After a desired number of passes of the same volume the ions may be allowed out of the ion mobility separator 1 for subsequent mass analysis.

The ion mobility separator 1 according to the preferred embodiment can advantageously operate at duty cycles approaching 100% as it can be arranged to eject only ions having a desired ion mobility whilst storing the other ions for further analysis. This is in contrast to a Field Asymmetric Ion Mobility Spectrometer (FAIMS) which is a scanning device whereby ions that are not transmitted are lost to the walls of the device.

A charge state separation device wherein a quadrupole is scanned in synchronisation with the output of a drift tube is the subject of a pending application. However, losses in ion transmission may occur as ions that enter the quadrupole with a stable trajectory may find themselves unstable part way through the quadrupole and so be lost.

An embodiment is contemplated wherein a quadrupole mass filter is provided downstream of a preferred ion mobility separator 1 and set to a discrete mass to charge ratio transmission window so as to match the desired mobility range ejected by the preferred ion mobility separator 1. This means that the desired ions are stable in the quadrupole mass filter all through the device. The equivalent to a scanning experiment can therefore be performed in a stepped manner with no loss in duty cycle as unejected ions are still stored by the ion mobility separator 1.

A conventional drift tube type of ion mobility spectrometer requires the use of a trapping stage in order to obtain a high duty cycle when using a continuous ion source. Ions may be admitted to the conventional drift tube ion mobility spectrometer using gate pulses which are narrow compared to drift times of ions. An ion mobility spectrometer that disperses ions on the millisecond timescale therefore requires a gate pulse of the order of microseconds in order to achieve the best resolution. The use of such gate pulses results in ion mobility discrimination at the entrance to the ion mobility spectrometer which results in reduced sensitivity and skewed spectra. In contrast, the ion mobility separator according to the preferred embodiment has no need for a narrow gate pulse as the ion mobility separator can be filled with a longer pulse of ions and so does not suffer from such problems which are inherent with conventional arrangements. An ion trap or other device for periodically releasing a pulse of ions into the ion mobility spectrometer 1 may nonetheless preferably be provided.

In addition to embodiments wherein a single transient DC potential or pulse Vg is translated along the length of the ion mobility separator 1, according to other embodiments a travelling DC voltage wave having a repeating waveform may be used to separate ions according to their ion mobilities. The amplitude and velocity of the one or more DC voltage waveforms may be arranged such that ions do not surf on a single voltage pulse along the drift region but instead roll over the top of subsequent pulses thereby receiving a succession of nudges leading to an overall drift in the wave direction. The transit time of an ion through the ion mobility separator 1 will therefore be dependent upon its ion mobility.

According to this embodiment a travelling wave ion guide may be used to provide the drift region. The ion guide may comprise either a stack of plates or a segmented multipole rod set. An ion trapping region upstream of the drift region may be provided with an ion gate to periodically pulse bunches of ions from the ion trap into the drift region.

Figure 9:
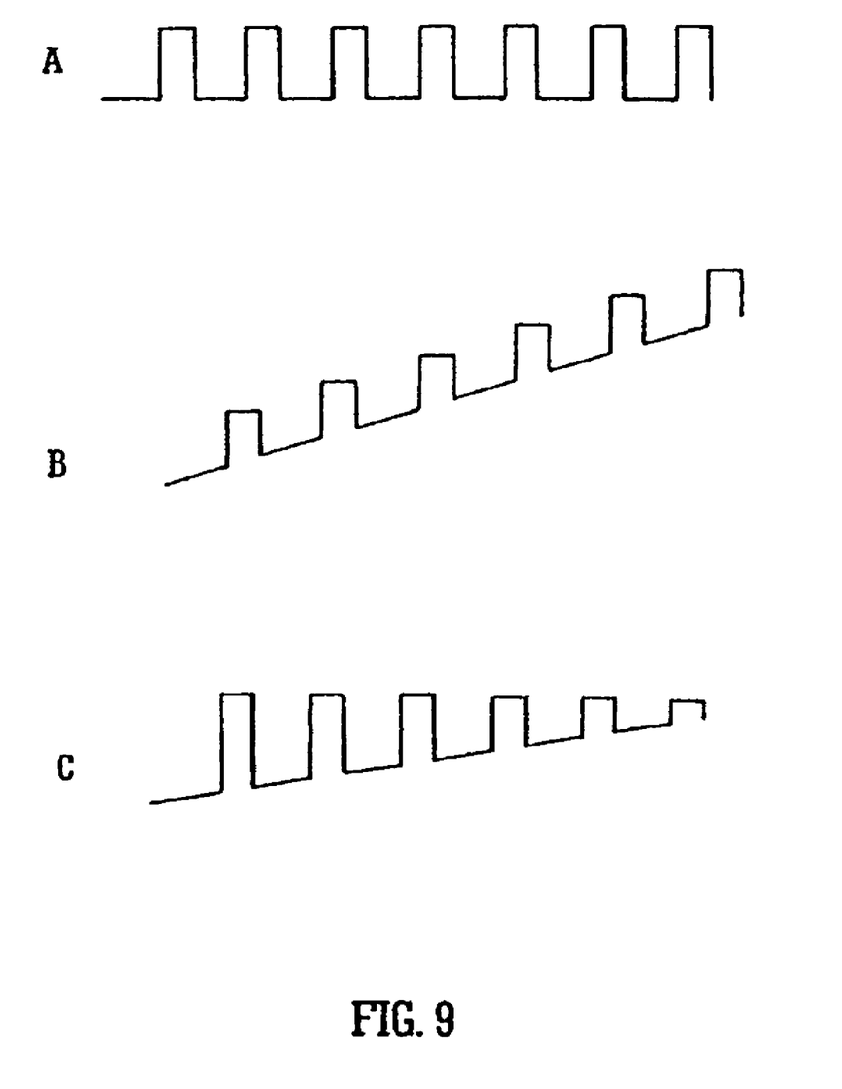
FIG. 9A shows a preferred travelling DC voltage waveform.
FIG. 9B shows another travelling DC voltage waveform and FIG. 9C shows a further travelling DC voltage waveform.

FIG. 9A shows a travelling DC voltage wave form having a periodic pulse of constant amplitude and velocity. FIG. 9B shows another DC potential waveform wherein a reverse DC gradient is superimposed on the travelling DC voltage waveform so that the field acts between pulses to move ions back towards the upstream ion gate or the entrance of the ion mobility separator 1. Such a DC voltage waveform may enhance the separation characteristics of the ion mobility separator 1 and may be used to prevent ions having an ion mobility less than a certain value from travelling with the travelling DC voltage wave and exiting the ion mobility separator 1. FIG. 9C shows a further DC potential waveform wherein the height of the voltage pulses reduces along the drift region as the potential due to an axial DC voltage gradient increases. Such a waveform may also enhance separation.

With the DC voltage waveform shown in FIG. 9C ions having a certain ion mobility may find balance points along the length of the drift region where the movement caused by the travelling DC voltage wave is counteracted by the reverse axial DC voltage gradient. Ions of different mobility may therefore find different balance points along the length of the ion mobility separator 1. A static mobility separation may therefore be produced and ions of similar mobility may collect in specific regions. These ions may be transmitted in a band-pass operation. The mode of operation using a voltage waveform as shown in FIG. 9C does not necessarily require an ion gate since it may operate with a continuous ion beam. Furthermore, the DC axial field may be constant or variable with position. This may be achieved by applying potentials to the electrodes forming the ion guide which increase linearly or non-linearly. Alternatively, the amplitude of the travelling DC voltage wave may decrease linearly or non-linearly as it progresses from the entrance to the exit of the ion mobility separator 1. The DC axial field and amplitude of the travelling wave may change with position. In one particular embodiment the DC axial field may continuously increase from the entrance to the exit of the ion mobility separator whilst the amplitude of the travelling DC voltage wave remains substantially constant.

The DC axial voltage gradient, the amplitude of the travelling wave and the velocity of the travelling DC voltage wave may also change with time. Hence, ions of differing mobility may first be separated spatially along the length of the ion guide and may then be moved along the ion mobility separator 1 to one end or the other. Ions may therefore be caused to exit the ion mobility separator 1 in increasing or decreasing order of their mobility.

Ions that have been separated according to their ion mobility may be caused to move to the exit of the ion mobility separator 1 by either reducing the DC potential gradient or by increasing the amplitude of the travelling DC voltage wave. These ions may also be moved to the exit of the ion mobility separator 1 by reducing the velocity of the travelling DC voltage wave or by reducing the gas pressure. Ions may also be caused to move by changing a combination of these controls. According to an embodiment ions may be caused to leave the ion mobility separator 1 in order of their ion mobility, starting with ions of highest mobility.

According to another embodiment the separated ions may be caused to move to the entrance of the ion mobility separator either by increasing the DC potential gradient and/or by reducing the amplitude of the travelling DC voltage wave and/or by increasing the velocity of the DC voltage wave and/or by increasing the gas pressure. According to this embodiment ions may be caused to be emitted from the ion mobility separator 1 via what was initially the entrance of the ion mobility separator 1 in order of their mobility starting with ions having the lowest ion mobility.

According to an embodiment the pulse amplitude, wave velocity, pressure and axial gradient may be varied during operation so as to enhance the separation.

Although the ion mobility separator 1 as described above may be used in isolation for the analysis of a substance by means of measurement of the mobility of its component parts, it may also be used for separation, collection and storage of components of a substance. The ion mobility separator 1 may form part of a mass spectrometer or a tandem mass spectrometer. The combination with a mass spectrometer provides a means of analysis with greater specificity. It also provides a means of separation, collection and storage of component fractions of a substance and therefore provides a means by which more components of a substance may be subsequently analysed in a mass spectrometer in greater detail.

A reversed axial voltage gradient may be used to enhance separation by constantly returning ions which have not been carried along by the travelling DC voltage wave to the entrance of the separation region.

Experimental data will now be presented. Ions were initially collected in an ion tunnel ion trap consisting of a stack of 90 ring electrodes each 0.5 mm thick and spaced apart by 1.0 mm. The central aperture of each ring was 5.0 mm diameter and the total length of the ion tunnel ion trap was 134 mm. A 2.1 MHz RF voltage was applied between neighbouring rings to radially confine the ion beam within the ion trap. Ions were retained in the ion tunnel ion trap by raising the DC potential at each end of the ion trap by approximately 5V. The pressure in the ion tunnel ion trap was about $10^{-3}$ mbar.

Ions were continuously generated using an Electrospray ion source and were continuously directed into the ion tunnel ion trap. The DC potential at the exit end of the ion trap was periodically reduced to allow ions to exit the ion trap. Ions were repeatedly collected and stored for 11 ms and then released over a period of 26 ns. Ions leaving the ion trap were accelerated through a 3 V potential difference and were then passed through a quadrupole rod set ion guide. The quadrupole was operating with only RF voltage applied to the rods so that is it was acting as an ion guide and not as a mass filter. The ions exiting the quadrupole rod set ion guide then entered an ion mobility separator 1 according to the preferred embodiment.

The ion mobility separator 1 consisted of a similar ion tunnel arrangement to that used for initially collecting and storing ions emitted from the ion source. The ion mobility separator 1 consisted of a stack of 122 ring electrodes, each 0.5 mm thick and spaced apart by 1.0 mm. The central aperture within each ring was 5.0 mm diameter and the total length of ring stack was 182 mm. A 2.4 MHz RF voltage was applied between neighbouring rings to radially confine the ions within the ion mobility separator 1. The pressure in the ion mobility separator 1 was approximately $2 \times 10^{-2}$ mbar. A travelling DC voltage wave was applied to the ion mobility separator 1 and consisted of a regular periodic pulse of constant amplitude and velocity.

The travelling DC voltage wave was generated by applying a DC voltage to a single ring electrode and every subsequent ring displaced by nine rings along the ring stack. Hence, one wavelength $\lambda$ of the DC voltage waveform consisted of one electrode with a raised DC potential followed by eight electrodes held at a lower (reference) potential. Thus the wavelength $\lambda$ was equivalent to the length of 9 electrodes or 13.5 mm and the total ion mobility separator was equivalent to approximately $13.5\lambda$. The travelling DC voltage wave was generated by applying approximately 0.65V to each ring electrode for 5 ns before moving the applied voltage to the next (adjacent) ring electrode. Thus the wave period or cycle time t was 45 ns. This was repeated uniformly along the length of the ion mobility separator 1. Thus the DC voltage wave velocity was equal to a constant 300 m/s.

At the exit of the ion mobility separator 1 the ions passed through a second quadrupole rod set. This was operated in an RF and DC mode (i.e. mass filtering mode) and was arranged to transmit ions having a particular mass to charge ratio. The ions were detected using an ion detector positioned downstream of the second quadrupole rod set.

Figure 10A:
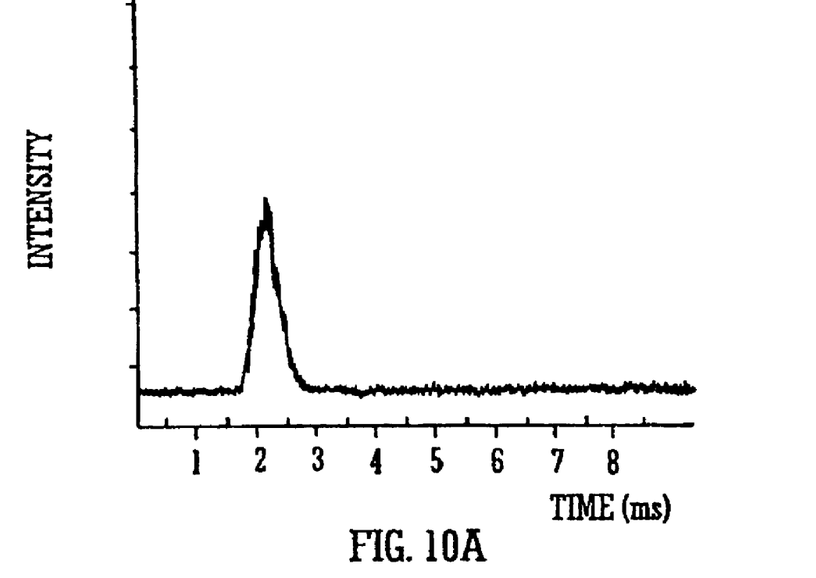
FIG. 10A shows the transit time recorded for Gramacidin-S (m/z 572) through a preferred ion mobility separator and FIG. 10B shows the transit time recorded for Leucine Enkephalin (m/z 556) through a preferred ion mobility separator.
Figure 10B:
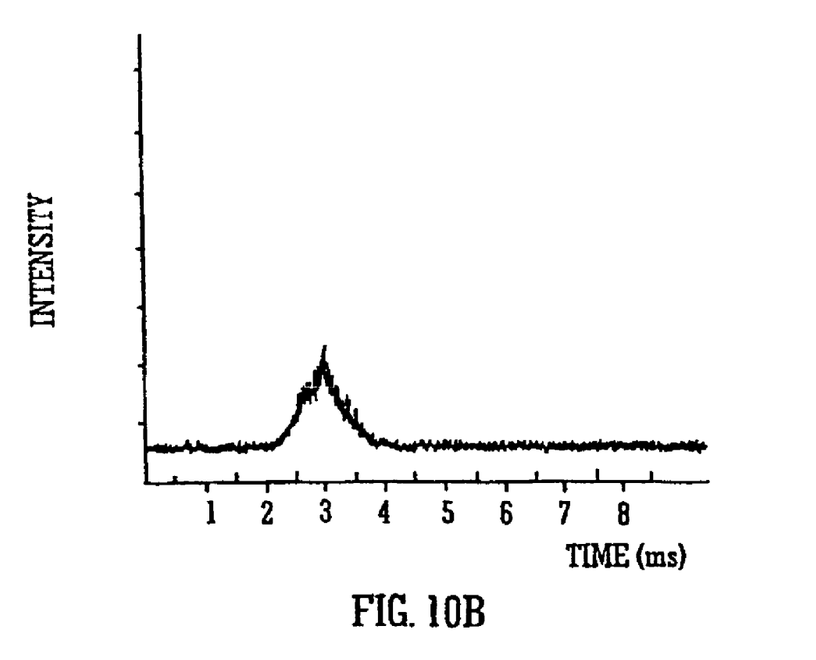

A mixture of Gramacidin-S (mol wt 1142 daltons) and Leucine Enkephalin (mol wt 555 daltons) were continuously introduced into an Electrospray ion source. Singly charged protonated ions of Leucine Enkephalin (m/z 556) and doubly charged protonated ions of Gramacidin-S (m/z 572) were collected and stored in the upstream ion trap. These ions were periodically released and their transit times to the ion detector were recorded and are shown in FIGS. 10A and 10B. For each measurement the second quadrupole mass filter was tuned to just transmit either m/z 556 for Leucine Enkephalin or m/z 572 for Gramacidin-S.

The trace for Gramacidin-S is shown in FIG. 10A and shows that the peak arrival time for ions was about 2.2 ms after release from the upstream ion trap. The corresponding trace for Leucine Enkephalin is shown in FIG. 10B and shows the corresponding peak arrival time was about 3.1 ms after release from the upstream ion trap. Timing cursors showed that the transit time for Gramacidin-S was about 940 ns less than that for Leucine Enkephalin. This is in spite of the fact that the m/z value for Gramacidin-S (572) is slightly greater than that for Leucine Enkephalin (556) and that the Gramacidin-S molecule (mol wt 1142 daltons) is also larger than the Leucine Enkephalin molecule (mol wt 555 daltons). However, shorter transit time for Gramacidin-S may be expected since the m/z 572 ion is doubly charged and experiences twice the force due to the electric field of the travelling wave than that experienced by the singly charged Leucine Enkephalin ion having m/z 556.

Although the doubly charged Gramicidin-S ion experienced twice the force it did not experience twice the viscous drag since its cross sectional area is not twice that of Leucine Enkephalin. It may be estimated that their relative cross sectional areas are in the ratio approximately $(1144/556)^{2/3}$ which is approximately 1.6. Hence the Gramacidin-S ion is more mobile than the Leucine Enkephalin ion in the presence of the same electric field and same high gas pressure. As a result, Gramacidin-S ions are more strongly affected by the travelling DC voltage waveform than Leucine Enkephalin ions. As a result, the transit time for Gramacidin-S ions through the ion mobility separator 1 was found to be less than that for Leucine Enkephalin. In fact the overall transit time for Gramacidin-S ions is less than that for Leucine Enkephalin despite the fact that the Leucine Enkephalin ions having lower mass to charge ratios will travel slightly faster through the two quadrupoles.

This experiment also demonstrates how two ions with substantially similar mass to charge ratios but having different charge states (z values) may be separated by the travelling wave ion mobility separator according to the preferred embodiment.

Although the present invention has been described with reference to preferred embodiments, it will be understood by those skilled in the art that various changes in form and detail may be made without departing from the scope of the invention as set forth in the accompanying claims.

What is claimed is:

1. An ion mobility separator wherein ions separate within said ion mobility separator according to their ion mobility and assume different essentially static or equilibrium axial positions along the length of said ion mobility separator.

2. An ion mobility separator as claimed in claim 1, wherein said ion mobility separator comprises a plurality of electrodes and wherein one or more transient DC voltages or one or more transient DC voltage waveforms are progressively applied to said electrodes so as to urge at least some ions in a first direction and wherein a DC voltage gradient acts to urge at least some ions in a second direction, said second direction being opposed to said first direction.

3. An ion mobility separator as claimed in claim 2, wherein the peak amplitude of said one or more transient DC voltages or said one or more transient DC voltage waveforms remains substantially constant or reduces along the length of the ion mobility separator.

4. An ion mobility separator as claimed in claim 2, wherein said DC voltage gradient progressively increases along the length of the ion mobility separator.

5. An ion mobility separator as claimed in claim 1, wherein once ions have assumed essentially static or equilibrium axial positions along the length of said ion mobility separator at least some of said ions are then arranged to be moved towards an exit of said ion mobility separator.

6. An ion mobility separator as claimed in claim 5, wherein at least some of said ions are arranged to be moved towards an exit of said ion mobility separator by: (i) reducing or increasing an axial DC voltage gradient; (ii) reducing or increasing the peak amplitude of said one or more transient DC voltages or said one or more transient DC voltage waveforms; (iii) reducing or increasing the velocity of said one or more transient DC voltages or said one or more transient DC voltage waveforms; or (iv) reducing or increasing the pressure within said ion mobility separator.

7. A mass spectrometer comprising an ion mobility separator as claimed in claim 1.

8. A method of ion mobility separation comprising causing ions to separate within an ion mobility separator and assume different essentially static or equilibrium axial positions along the length of the ion mobility separator.

9. A method of ion mobility separation as claimed in claim 8, wherein said ion mobility separator comprises a plurality of electrodes and wherein one or more transient DC voltages or one or more transient DC voltage waveforms are progressively applied to said electrodes so as to urge at least some ions in a first direction and wherein a DC voltage gradient acts to urge at least some ions in a second direction, said second direction being opposed to said first direction.

10. A method of ion mobility separation as claimed in claim 9, wherein the peak amplitude of said one or more transient DC voltages or said one or more transient DC voltage waveforms remains substantially constant or reduces along the length of the ion mobility separator.

11. A method of ion mobility separation as claimed in claim 9, wherein said DC voltage gradient progressively increases along the length of the ion mobility separator.

12. A method of ion mobility separation as claimed in claim 8, wherein once ions have assumed essentially static or equilibrium axial positions along the length of said ion mobility separator at least some of said ions are then arranged to be moved towards an exit of said ion mobility separator.

13. A method of ion mobility separation as claimed in claim 12, wherein at least some of said ions are arranged to be moved towards an exit of said ion mobility separator by: (i) reducing or increasing an axial DC voltage gradient; (ii) reducing or increasing the peak amplitude of said one or more transient DC voltages or said one or more transient DC voltage waveforms; (iii) reducing or increasing the velocity of said one or more transient DC voltages or said one or more transient DC voltage waveforms; or (iv) reducing or increasing the pressure within said ion mobility separator.

14. A method of mass spectrometry comprising the method of ion mobility separation as claimed in claim 8.

* * * * *

UNITED STATES PATENT AND TRADEMARK OFFICE
CERTIFICATE OF CORRECTION

PATENT NO. : 6,914,241 B2
DATED : July 5, 2005
INVENTOR(S) : Giles et al.

It is certified that error appears in the above-identified patent and that said Letters Patent is hereby corrected as shown below:

Title page,
Item [75], Inventors, should read as follows:
-- Kevin Giles, Altrincham, United Kingdom
  John Brian Hoyes, Stockport, United Kingdom
  Steve Pringle, Hoddleston, United Kingdom
  Jason Lee Wildgoose, United Kingdom
  Robert Harold Bateman, Cheshire, United Kingdom --.

Signed and Sealed this

Twenty-first Day of March, 2006

JON W. DUDAS
*Director of the United States Patent and Trademark Office*